United States Patent [19]

Nielsen

[11] Patent Number: 6,151,123
[45] Date of Patent: Nov. 21, 2000

[54] SYSTEMS AND METHODS FOR EMPLOYING OPTICAL PROBES TO CHARACTERIZE MATERIAL PROPERTIES

[75] Inventor: Ralph B. Nielsen, San Jose, Calif.

[73] Assignee: Symyx Technologies, Inc., Santa Clara, Calif.

[21] Appl. No.: 09/112,247

[22] Filed: Jul. 8, 1998

Related U.S. Application Data

[60] Provisional application No. 60/052,468, Jul. 14, 1997.

[51] Int. Cl.$^7$ .................................................. G01N 21/55
[52] U.S. Cl. ............................................................ 356/445
[58] Field of Search ................................... 356/445–448, 356/337, 338, 343

[56] References Cited

U.S. PATENT DOCUMENTS

| | | | |
|---|---|---|---|
| 5,143,854 | 9/1992 | Pirrung et al. | 436/518 |
| 5,361,734 | 11/1994 | Shirai | 123/90.16 |
| 5,424,186 | 6/1995 | Fodor et al. | 435/6 |
| 5,874,219 | 2/1999 | Rava et al. | 435/6 |

FOREIGN PATENT DOCUMENTS

| | | | |
|---|---|---|---|
| WO 90/15070 | 12/1990 | WIPO | C07K 1/04 |
| WO 92/10092 | 6/1992 | WIPO | A01N 1/02 |

OTHER PUBLICATIONS

"A Combinatorial Approach for Polymer Design," J. S. Brocchini, K. James, V. Tangpasuthadol, J. Kohn, *Journal of the American Chemical Society*, vol. 119, pp. 4553–4554, 1997.

"High–Conversion Polymerization Fluorescence Probes. 1. Polymerization of Methyl Methacrylate," Rafik O. Loutfy, *Macromolecules*, vol. 14, pp. 270–275, 1981.

"Solvent and Temperature Effects on the Decay Dynamics of [p–N,N–(Dialkylamino)Benzylidene]Malononitriles", A. Safarzadeh–Amiri, *Chemical Physical Letters*, vol. 129, No. 3, pp. 225–230, 1986.

"Strategies for Epitope Analysis Using Peptide Synthesis," H. Mario Geysen etal., *Journal of Immunological Methods*, vol. 102, pp. 259–274, 1987.

*Primary Examiner*—Frank G. Font
*Assistant Examiner*—Michael P. Stafira

[57] ABSTRACT

Methods and apparatus for screening diverse arrays of materials are provided. In particular, the present invention provides techniques for interrogating organic materials, inorganic materials, or polymers on predefined regions of a substrate, using optical probe molecules to measure properties of these materials. This invention involves the use of environment-sensitive probes, such as dye probes, to enable parallel, rapid and efficient characterization of important material properties, including glass-transition temperatures, polarity, hydrogen bonding and other intermolecular interactions. These methods can be applied to crystalline or amorphous materials, polymeric or small-molecule materials, pure materials or mixtures, and to materials in bulk, particles, thin films, dispersions, emulsions, and solutions.

34 Claims, 4 Drawing Sheets

DYE 1

DYE 2

SYSTEMS AND METHODS FOR EMPLOYING OPTICAL PROBES TO CHARACTERIZE MATERIAL PROPERTIES

This application claims benefit of provisional application Ser. No. 60/052,468 Jul. 14, 1997.

CROSS REFERENCE TO RELATED APPLICATIONS

This application is related to commonly assigned provisional application entitled "Systems and Methods for the Rapid Characterization of Libraries of Materials", Ser. No. 60/050,949, filed Jun. 13, 1997 (Attorney Docket No. 16703-000900), the complete disclosure of which is incorporated herein by reference for all purposes. This application is also related to commonly assigned, co-pending U.S. patent applications Ser. Nos. 08/327,513, filed Oct. 18, 1994 (Attorney Docket No. 14939-000400), 08/438,043, filed May 8, 1995 (Attorney Docket No. 14939-000410), and PCT Application No. WO 95/13278, filed Oct. 18, 1995 (Attorney Docket No. 14939-000400PC), the complete disclosures of which are incorporated herein by reference for all purposes. This application is also related to commonly assigned, co-pending U.S. Patent Application entitled "THE COMBINATORIAL SYNTHESIS OF NOVEL MATERIALS", concurrently filed with this application on Apr. 22, 1997 (Attorney Docket No. 16703-000700), the complete disclosure of which is incorporated herein by reference for all purposes.

FIELD OF THE INVENTION

The present invention generally relates to methods and apparatus for rapidly characterizing or screening an array of diverse materials which have been created at known locations on a single substrate surface. This screening may be for a variety of measurable properties of many classes of materials including but not limited to organic materials, polymers and inorganic materials. The invention involves the use of environment-sensitive probes, such as dye probes, to enable parallel, rapid and efficient characterization of important material properties, including glass-transition temperatures, polarity, hydrogen bonding and other intermolecular interactions. The methods of the present invention can be applied to crystalline or amorphous materials, polymeric or small-molecule materials, pure materials or mixtures, and to materials in bulk, particles, thin films, dispersions, emulsions, and solutions.

BACKGROUND OF THE INVENTION

The discovery of new materials with novel chemical and physical properties often leads to the development of new and useful technologies. Currently, there is a tremendous amount of activity in the discovery and optimization of materials, such as superconductors, zeolites, magnetic materials, phosphors, nonlinear optical materials, thermoelectric materials, high and low dielectric materials and the like. Unfortunately, even though the chemistry of extended solids has been extensively explored, few general principles have emerged that allow one to predict with certainty the composition, structure and reaction pathways for the synthesis of such solid state compounds.

The preparation of new materials with novel chemical and physical properties is at best happenstance with our current level of understanding. Consequently, the discovery of new materials depends largely on the ability to synthesize and analyze new compounds. Given approximately 100 elements in the periodic table which can be used to make compositions consisting of three, four, five, six or more elements, the universe of possible new compounds remains largely unexplored. As such, there exists a need in the art for a more efficient, economical and systematic approach for the synthesis of novel materials and for the screening of such materials for useful properties.

One of the processes whereby nature produces molecules having novel functions involves the generation of large collections (libraries) of molecules and the systematic screening of those collections for molecules having a desired property. An example of such a process is the humoral immune system which in a matter of weeks sorts through some $10^{12}$ antibody molecules to find one which specifically binds a foreign pathogen (Nisonoff, et al., *The Antibody Molecule* (Academic Press, New York, 1975)). This notion of generating and screening large libraries of molecules has recently been applied to the drug discovery process. The discovery of new drugs can be likened to the process of finding a key which fits a lock of unknown structure. One solution to the problem is to simply produce and test a large number of different keys in the hope that one will fit the lock.

Using this logic, methods have been developed for the synthesis and screening of large libraries (up to $10^{14}$ molecules) of peptides, oligonucleotides and other small molecules. Geysen, et al., for example, have developed a method wherein peptide syntheses are carried out in parallel on several rods or pins (see, *J. Immun. Meth.* 102:259–274 (1987), incorporated herein by reference for all purposes). Generally, the Geysen, et al. method involves functionalizing the termini of polymeric rods and sequentially immersing the termini in solutions of individual amino acids. In addition to the Geysen, et al. method, techniques have recently been introduced for synthesizing large arrays of different peptides and other polymers on solid surfaces. Pirrung, et al., have developed a technique for generating arrays of peptides and other molecules using, for example, light-directed, spatially-addressable synthesis techniques (see, U.S. Pat. No. 5,143,854 and PCT Publication No. WO 90/15070, incorporated herein by reference for all purposes). In addition, Fodor, et al. have developed, among other things, a method of gathering fluorescence intensity data, various photosensitive protecting groups, masking techniques, and automated techniques for performing light-directed, spatially-addressable synthesis techniques (see, Fodor, et al., PCT Publication No. WO 92/10092, the teachings of which are incorporated herein by reference for all purposes).

Using these various methods, arrays containing thousands or millions of different elements can be formed (see, U.S. patent application Ser. No. 08/805,727, filed Dec. 6, 1991, the complete disclosure of which is incorporated herein by reference for all purposes). As a result of their relationship to semiconductor fabrication techniques, these methods have come to be referred to as "Very Large Scale Immobilized Polymer Synthesis," or "VLSIPS™" technology. Such techniques have met with substantial success in, for example, screening various ligands such as peptides and oligonucleotides to determine their relative binding affinity to a receptor such as an antibody.

The solid phase synthesis techniques currently being used to prepare such libraries involve the stepwise, i.e., sequential, coupling of building blocks to form the compounds of interest. In the Pirrung, et al. method, for example, polypeptide arrays are synthesized on a substrate by attaching photoremovable groups to the surface of the substrate, exposing selected regions of the substrate to light to activate those regions, attaching an amino acid monomer with a photoremovable group to the activated region, and repeating the steps of activation and attachment until polypeptides of the desired length and sequences are synthesized. These solid phase synthesis techniques, which involve the sequential coupling of building blocks (e.g., amino acids) to form the compounds of interest, cannot readily be used to prepare many inorganic and organic compounds.

Schultz, et al. apply combinatorial chemistry techniques to the field of material science (PCT WO 96/11878, the complete disclosure of which is incorporated herein by reference). More particularly, Schultz, et al. provide methods and apparatus for the preparation and use of a substrate having an array of diverse materials in predefined regions thereon. A substrate having an array of diverse materials thereon is generally prepared by delivering components of materials to predefined regions on the substrate to form different materials. Using the methodology of Schultz, et al., many classes of materials can be generated combinatorially including, for example, inorganic materials, intermetallic materials, metal alloys, ceramic materials, etc. Once prepared, such materials can be screened for useful properties including, for example, electrical, thermal, mechanical, etc.

In the field of pharmaceutical research, high-throughput screening (HTS) protocols have existed for some time for the screening of natural products and archived synthetic libraries. The development of synthetic methods for creating large libraries of organic molecules with possible pharmaceutical relevance has been the final piece of the pharmaceutical combinatorial puzzle, generating much of the recent excitement. While important, the ability to rapidly prepare libraries of polymers is of little value without the ability to rapidly screen materials for properties of interest. This combination of synthetic and screening strategies significantly alters the discovery process for polymers in many commercially important applications, including bulk plastics, imaging systems, thin polymer films, adhesives, polymers for electronic or optical devices, and coatings.

Many aspects of polymer science are well adapted to combinatorial research strategies. Since polymers are generally synthesized from individual monomer units, parallel synthesis strategies, including combinatorial synthesis, will allow exploration of polymer composition by direct combination of different monomers. For practical commercial applications, however, polymer discovery usually requires far more information than the monomer composition alone. Included in this are physical attributes such as hydrogen bonding and other interchain interactions, chain orientation, processing effects, microphase separation, polarity, glass transition temperature, solubility, miscibility, chain mobility, melting temperature, degree of crystallinity, free volume, and physical aging. The effective application of combinatorial methods to polymer science and organic materials discovery requires rapid sample preparations and screening protocols for these properties.

Dyes of various types have been used to probe the attributes of individual chemical and biological systems. Such probes can provide information based on effects of the system of interest on spectral attributes or intensity of dye absorption or fluorescent emission. Such probes can be physically combined with the system of interest, or can be covalently or ionically bound to the system. Some environmentally sensitive dyes provide information related to the system of interest based on dye-dye interactions, while others provide information directly related to the microenvironment of separated dye molecules. One particularly interesting system is based on dyes that link donor fragments and acceptor fragments with a flexible link, typified by the molecule 4-(dimethylaminobenzylidene)malononitrile, and substituted variants. With dyes of this sort, fluorescent behavior of the dye may be affected by the microviscosity of the environment, with viscous environments tending to increase fluorescent quantum yield. (Loutfy, R. O. *Macromolecules,* 1981, 14, 270–275. Safarzadeh-Amiri, A. *Chem. Phys. Lett,* 1986, 129, 225, the complete disclosure of which is incorporated herein by reference for all purposes.) The fluorescence can be strongly influenced by temperature, solvent, and environment polarity. It has been shown in one case that the temperature dependence of the fluorescence of a related dye imbedded in a poly(methylmethacrylate) matrix showed a distinct break at the $T_g$ of the polymer matrix. (Loutfy.) One very recent report has described the preparation of a 112 member polymer library as a candidate pool for selecting biomedical implant materials. (Brocchini, S.; James, K.; Tangpasuthadol, V.; Kohn, J. *J. Am. Chem. Soc.* 1997, 119, 4553–4554.) This library design also allowed for the elucidation of useful structure property relationships. However, this work does not address the need for efficient and rapid characterization of polymers. Conventional, time-consuming characterization of each individual material was carried out, including the use of differential scanning calorimetry (DSC) to measure $T_g$ of each material, a technique that typically requires between 30 minutes to one hour per sample. With the ability to rapidly create many materials in a combinatorial array, such slow, sequential analytical methods become rate-limiting in the materials discovery process. To this end, it would be beneficial to construct apparatus and methodology for screening a substrate having an array of materials that differ slightly in composition, concentrations, stoichiometries and thickness across the substrate.

SUMMARY OF THE INVENTION

The present invention provides methods and apparatus for interrogating a substrate having an array of diverse materials in predefined regions thereon. More specifically, the invention is directed to systems and methods for measuring or characterizing the absolute and relative properties of materials in parallel (or sequentially in a rapid, scanning manner). The materials screened in the present invention include polymeric materials, organic materials, amorphous materials, crystalline materials, small-molecule materials, inorganic materials, phosphor materials, pure materials, mixtures of materials, bulk materials, particles of materials, thin films of materials, dispersions of materials emulsions of materials, and solutions of materials.

In one aspect of the invention, an array of materials is combined with at least one environment-sensitive optical probe on a substrate such that each material is located with the optical probe at a predefined location on the substrate. The environment-sensitive optical probes can be dyes, inorganic phosphors, etc. The optical behavior of the probes are monitored in parallel (or in series) to characterize or measure one or more properties of each material. In some embodiments, light is directed onto the optical probes and materials within the array and the environment around the substrate is varied. The optical properties of each material are then measured as a function of the varied environment.

In preferred embodiments of the present invention, an array of multiple samples of materials is characterized by combining each material with a dye, illuminating the samples and varying the temperature of the substrate. A property (e.g., glass transition temperature) of each sample is measured as a function of temperature. In one embodiment, the temperature of the substrate is varied over a range that includes the absolute glass transition temperature of the materials, and the intensity of the fluorescent emissions of each optical probe is measured to determine the relative glass transition temperatures of each material within the array.

The present invention enables the screening, or optical measurement of various physical or chemical properties, of at least 5 materials, alternatively, the screening of at least 10 materials, alternatively, the screening of at least 20 materials, alternatively, the screening of at least 50 materials, alternatively the screening of at least 100 materials, alternatively, the screening of at least 500 materials, alternatively, the screening of at least 1,000 materials. For some materials, the present invention enables the screening of at least 10,000 materials, alternatively of at least 100,000 materials and alternatively of at least 1,000,000 materials. Properties that can be screened for include glass transition temperature, polarity, hydrogen bonding as well as other intermolecular interactions.

The present invention also provides systems for rapidly screening an array of materials at known locations on a substrate. Such systems include at least one environment-sensitive optical probe combined with each of the materials to form library elements at predefined locations on a substrate, a light source for illuminating each library element and an optical measurement system for monitoring the optical properties of the probes to characterize or measure one or more properties of each material. The system further includes a device for controlling the environment of the substrate so that the properties of each material can be measured as a function of the controlled environment.

In preferred embodiments of this system, the environmental-sensitive optical probe comprises a dye, and controlling the environment is achieved by varying the temperature of the system. In other preferred embodiments, optical measurement systems are used to measure, for example fluorescence intensity and other optical characteristics. These systems may include but are not limited to a CCD measuring systems, UV measuring systems, a visible measuring systems, IR measuring systems or the like. The use of either rapid-scan optics or parallel sensors such as CCD focal plane arrays should allow for many samples to be rapidly characterized in dense library formats.

The present invention provides a number of advantage. Since optical probe molecules can be sensitive to Tg, polarity, etc., they can be applied to screen large numbers of materials in parallel. This technique provides a significant time saving advantage. Typically, a single Tg measurement by differential scanning calorimetry (DSC) requires about 10 mg of polymer, several minutes of sample preparation, (using tedious, manual loading of small, expensive sealable metal pans), and approximately 30–60 minutes or more for 2 heating ramps. The methods of the present invention typically require less than 60 minutes for 96 samples and often less than 30 minutes for 96 samples. In principle, this technique can be used to screen 1000 samples in 10 minutes or less, an acceleration of about 10,000 times the current state of the art. Also, the method described herein may be more precise than DSC, because the optical probes respond instantly to the environment, while heating the DSC sample and measuring differential heat flow has substantial delay in the system, limiting precision of the measurement.

In addition, the present invention requires very little sample, compared to DSC, with about 50 micrograms polymer and about 0.25 micrograms dye per sample used in the examples described. This allows very rapid heating and excellent thermal control of the sample. The method of the present invention requires a simple apparatus which includes a heated plate that can be observed using a camera, offering easily controlled environments of the sample (e.g. humidity, solvent vapors, vacuum, pressure, etc.,) as compared to the heat-flow cell of a complicated calorimeter.

Finally, this invention enables the screening of materials on a wide number of different substrates, or in the presence of other components or materials without interference. This is because the substrate does not substantially interfere with the measurement of the materials thereon, using the methods of the present invention. By contrast, calorimetry generally loses sensitivity when other large objects (or objects having relatively high heat capacities) are included in the DSC sample.

A further understanding of the nature and advantages of the inventions herein may be realized by reference to the remaining portions of the specification and the attached drawings.

DETAILED DESCRIPTION OF THE INVENTION AND PREFERRED EMBODIMENTS

I. Glossary

Figure 1:
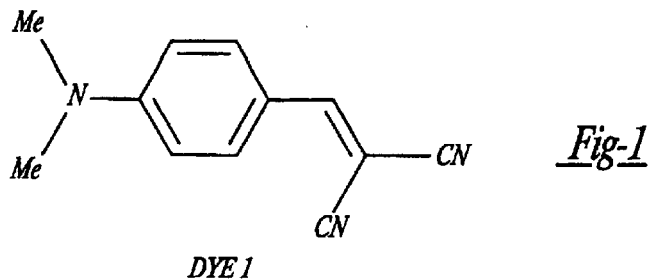
FIG. 1 illustrates the chemical structure of a first dye used as an optical probe in the methods of the present invention.

The following terms are intended to have the following general meanings as they are used herein.

1. Substrate: A material having a rigid or semi-rigid surface. In many embodiments, at least one surface of the substrate will be substantially flat, although in some embodiments it may be desirable to physically separate synthesis regions for different materials with, for example, dimples, wells, raised regions, etched trenches, or the like. In some embodiments, the substrate itself contains wells, raised regions, etched trenches, etc. which form all or part of the synthesis regions. According to other embodiments, small beads or pellets may be provided on the surface within dimples or on other regions of the surface or, alternatively, the small beads or pellets may themselves be the substrate. The substrate will typically have a surface area of about 1 to 400 $cm^2$, usually about 6 to 100 $cm^2$. However, it should be understood that the substrate may be substantially smaller or larger than these ranges depending on the particular application. For example, the substrate may have a surface area as small as about 0.1 to 1 $cm^2$, or as large as about 1 to 100.

2. Predefined Region: A predefined region is a localized area on a substrate which is, was, or is intended to be used for formation of a selected resulting material and is otherwise referred to herein in the alternative as "known" region, "reaction" region, a "selected" region, or simply a "region." The predefined region may have any convenient shape, e.g., linear, circular, rectangular, elliptical, wedge-shaped, etc. Additionally, the predefined region, i.e., the reaction site, can be a bead or pellet which is coated with component(s) of interest. In this embodiment, the bead or pellet can be identified with a tag, such as an etched binary bar code that can be used to indicate the history of the bead or pellet, i.e., to identify which components were deposited thereon. In some embodiments, a predefined region and, therefore, the area upon which each distinct material is synthesized is smaller than about 25 cm$^2$, less than 10 cm$^2$, less than 5 cm$^2$, even more less than 1 cm$^2$, still more less than 1 mm$^2$, and less than 0.5 mm$^2$. In most preferred embodiments, the regions have an area less than about 10,000 $\mu$m$^2$, less than 1,000 $\mu$m$^2$, less than 100 $\mu$m$^2$, and less than 10 $\mu$m$^2$.

3. Radiation: Energy which may be selectively applied including energy having a wavelength between $10^{-14}$ and $10^4$ meters including, for example, electron beam radiation, gamma radiation, x-ray radiation, ultraviolet radiation, visible light, infrared radiation, microwave radiation and radio waves. "Irradiation" refers to the application of radiation to a surface.

4. Mixture or Blend: The term "mixture" or, interchangeably, "blend" refers to a collection of molecules, ions, electrons, chemical substances, etc. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

5. Layer: The term "layer" is used herein to refer to a material that separates one material, component, substrate or environment from another. A layer is often thin in relation to its area and covers a material beneath it. A layer may or may not be thin or flat, but once it is deposited it generally covers the entire surface such that it separates the component or substrate below the layer from the component or atmosphere above the layer. A layer may be a flat, thin section of material which can have similar flat sections above and below it. The layers are thin in relation to their area and may cover all or part of the material beneath them.

II. General Overview

The present invention relates to methods and apparatus for rapidly characterizing or screening arrays of materials for physical and chemical properties, in particular, organic materials, polymers and inorganic materials, that have been created at known locations on a substrate surface. This invention involves the use of environment-sensitive probes, for example dye probes, to enable parallel, rapid and efficient characterization of important material properties, including glass-transition temperatures, polarity, hydrogen bonding and other intermolecular interactions. These methods can be applied to crystalline or amorphous materials, polymeric or small-molecule materials, inorganic materials, phosphors, pure materials or mixtures, and to materials in bulk, particles, thin films, dispersions, emulsions, and solutions. The arrays of materials characterized using the methods described in this invention, are produced using parallel synthesis techniques (or sequential synthesis with rapid scan optics), including but not limited to, combinatorial synthesis. Substrates that can be used in this invention can include but are not limited to, glass, silicon, metals, ceramics, etc.

Preferred embodiments of the present invention provide methods and apparatus for rapidly screening an array of, for example, organic materials, inorganic materials, or polymers in predefined regions on a substrate, using optical probe molecules to measure properties of these materials. These properties include glass transition temperatures ($T_g$) and other properties related to the microenvironment of the probe molecule, such as polarity, degree of intermolecular interactions such as hydrogen bonding, free volume changes associated with physical aging, and polarity. These measurements can be achieved by preparing a large number of samples of the material or polymer of interest within predefined regions of a substrate, together with a small amount of a relevant dye or dye-mixture, and then exposing the samples and substrate to conditions (e.g., temperature, pressure humidity, polarity, atmosphere variations, and the like) relevant to the material's property of interest while monitoring the optical behavior of the molecular dye probes at each pre-defined area of the array. Dye probes are present at concentrations low enough so as not to interfere with the properties of the materials that are being measured, while having sufficient concentration to emit detectable fluorescence. Those of ordinary skill in the art will recognize that these concentration can be found through routine experimentation.

Because optical probe molecules are sensitive to Tg, polarity, etc., they can be applied to screen large numbers of materials in parallel (or sequentially with rapid scan optics). This invention provides a method for rapidly characterizing or screening arrays of multiple materials or polymers for physical and chemical properties, wherein samples of the materials or polymers have been created at known locations on a substrate surface. The materials or polymers can be combined with at least one environment-sensitive dye or optical probe, and the optical properties of the dye or optical probe are observed under conditions that allow the parallel or sequential measurement of the absolute or relative properties of the materials or polymers in the array. This invention enables the parallel or rapid sequential screening (i.e., optical measurement of various physical or chemical properties) of at least 5 materials, alternatively, the screening of at least 10 materials, alternatively, the screening of at least 20 materials, alternatively, the screening of at least 50 materials, alternatively the screening of at least 100 materials, alternatively, the screening of at least 500 materials, alternatively, the screening of at least 1,000 materials. For at least some materials, the present invention enables the screening of at least 10,000 materials, alternatively of at least 100,000 materials and alternatively of at least 1,000,000 materials.

Figure 4A:
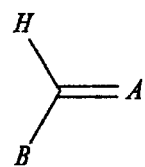
FIGS. 4A–4C illustrate representative chemical structures of starting material fragments for dye structures.
Figure 4B:
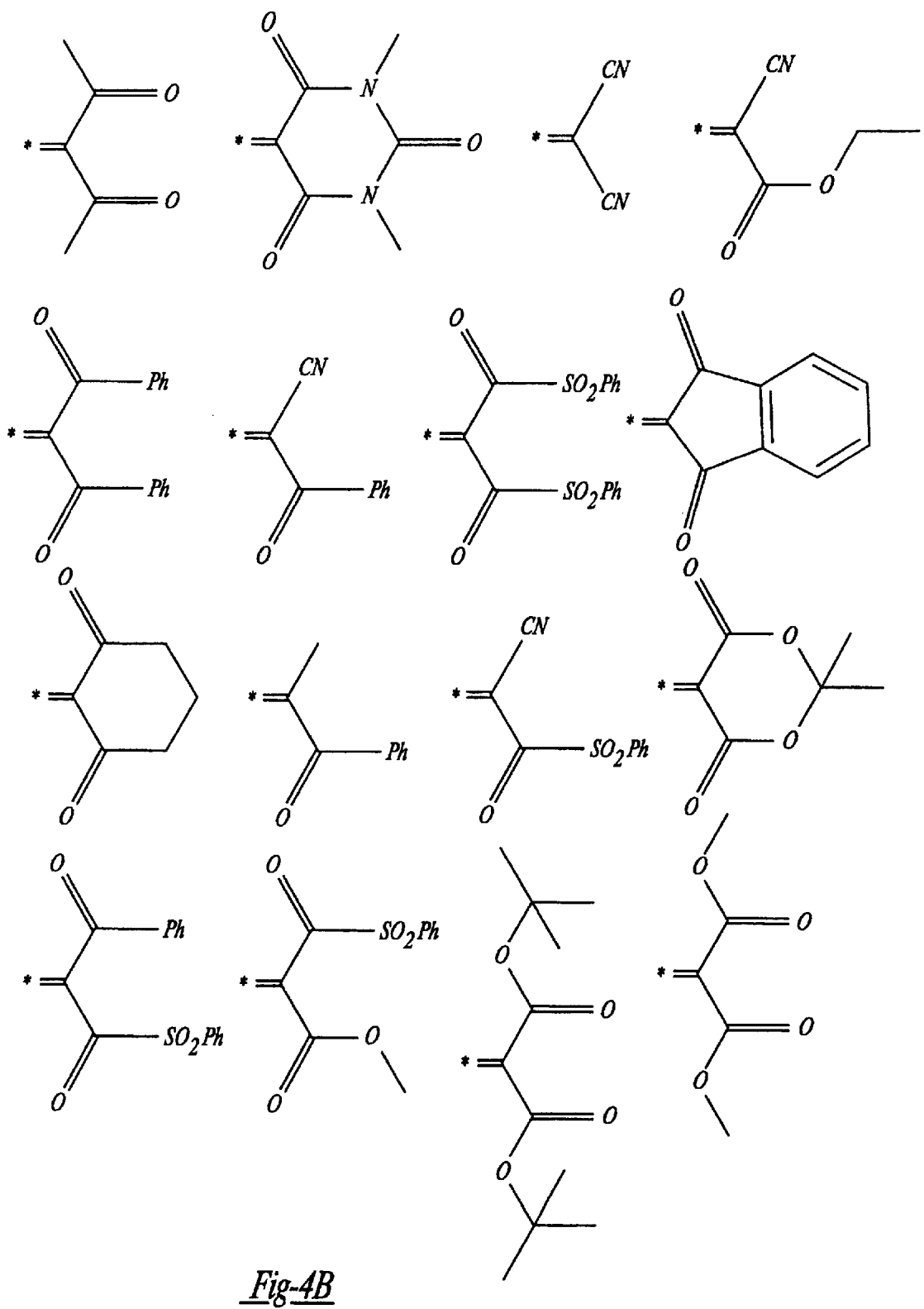
Figure 4C:
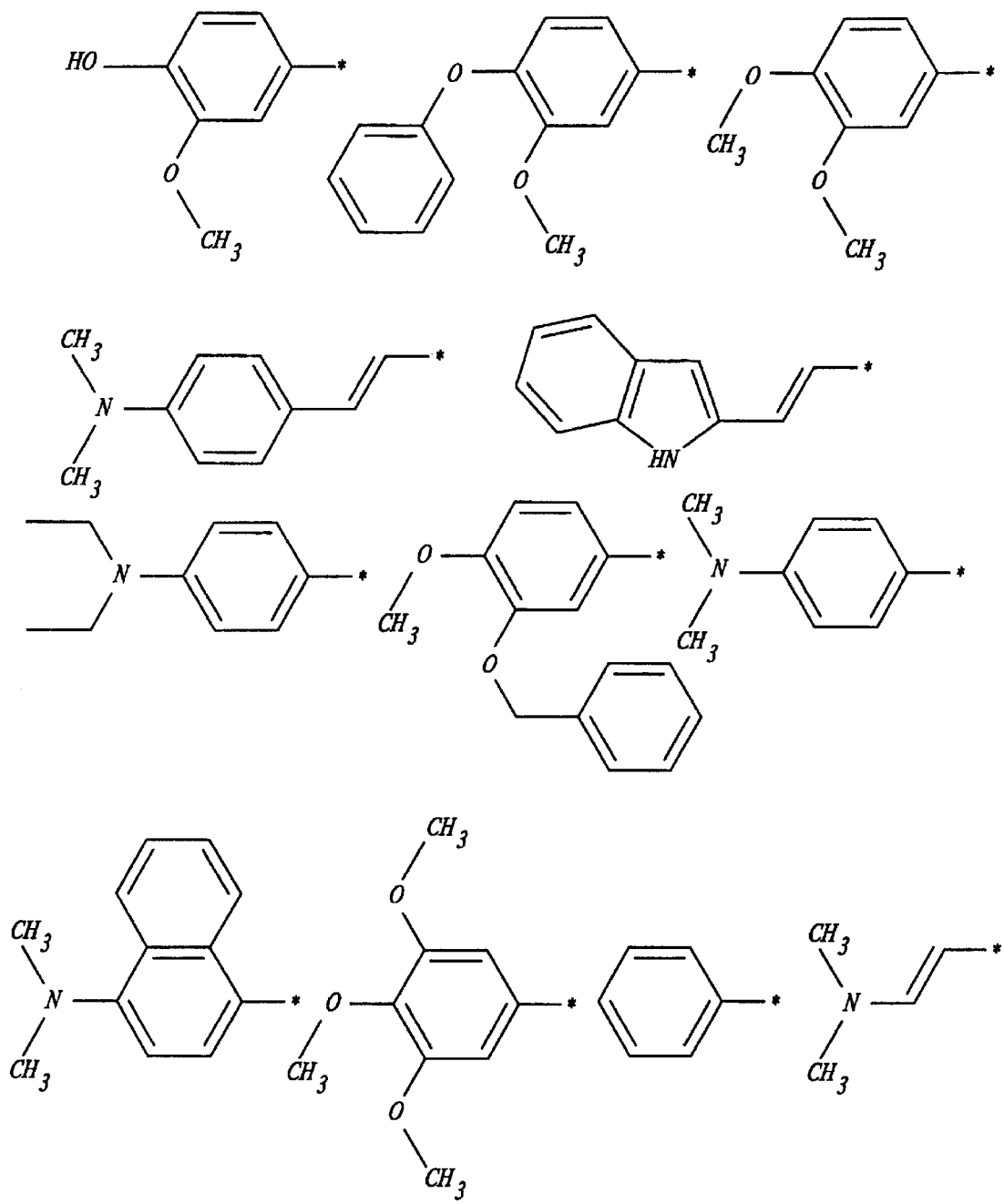

Suitable dyes for use with the present invention are shown in FIGS. 4A–4C. FIG. 4a illustrates the generic structure, and examples of A and B are shown in FIGS. 4B and 4C, respectively. In FIG. 4B, the asterisk is on the double bond of the generic. In FIG. 4C, the asterisk is on the single bond between B and the generic structure.

In addition, the techniques of the present invention allow arrays of materials to be screened rapidly and precisely. Usually, the measurement, i.e., Tg measurements with good precision, will take less than about 10 minutes analysis time/material, often less than about 5 minutes/per material and typically less than 1 minute analysis time/material sample.

In one embodiment of this invention, the glass-transition temperatures of multiple polymers or organic materials are measured simultaneously (or sequentially) by preparing a spatially defined array of polymer films containing less than about 1.0% by weight of a dye on a glass substrate. The substrate and array of materials are then subjected to a temperature ramp that includes the glass transition temperatures of the polymers or organic materials while simultaneously (or sequentially, e.g., scanning) illuminating the samples with irradiation of the appropriate wavelength. The intensity of the fluorescent emission from each element is measured with a sensor array, such as a charge-coupled device (CCD) camera. The $T_g$ of the various component materials may then be deduced by the variation of emission intensity with temperature, and the relative $T_g$ of each material in the array can be quickly and precisely measured.

In another embodiment of the invention, free-volume changes that occur after amorphous polymeric or amorphous organic samples are quenched below $T_g$ and allowed to age are measured. In this embodiment, a similarly prepared array of films is subjected to appropriate conditions of quenching, followed by measurement of the fluorescent emission intensity of the films at appropriate times after the quench process. Samples with larger physical aging will exhibit a greater increase in fluorescent emission. Similarly, the effects of humidity or solvent vapor on multiple materials on $T_g$ or physical aging kinetics can be simultaneously (or sequentially) measured by performing the measurements described above under conditions of differing humidity of solvent vapor concentration.

Similar strategies, with the proper dye probes, can rapidly screen multiple materials for differences in polarity, hydrogen bonding capability, or other attributes of interest. Also, miscibility of mixtures may be evaluated by preparing mixtures and examining them by the methods described. Microphase separated mixtures exhibit multiple transition temperatures, while miscible systems exhibit a single glass transition. This can be useful for characterization of polymer blends, mixtures of polymers and additives, and phase separation behavior of block copolymer systems.

Figure 5:
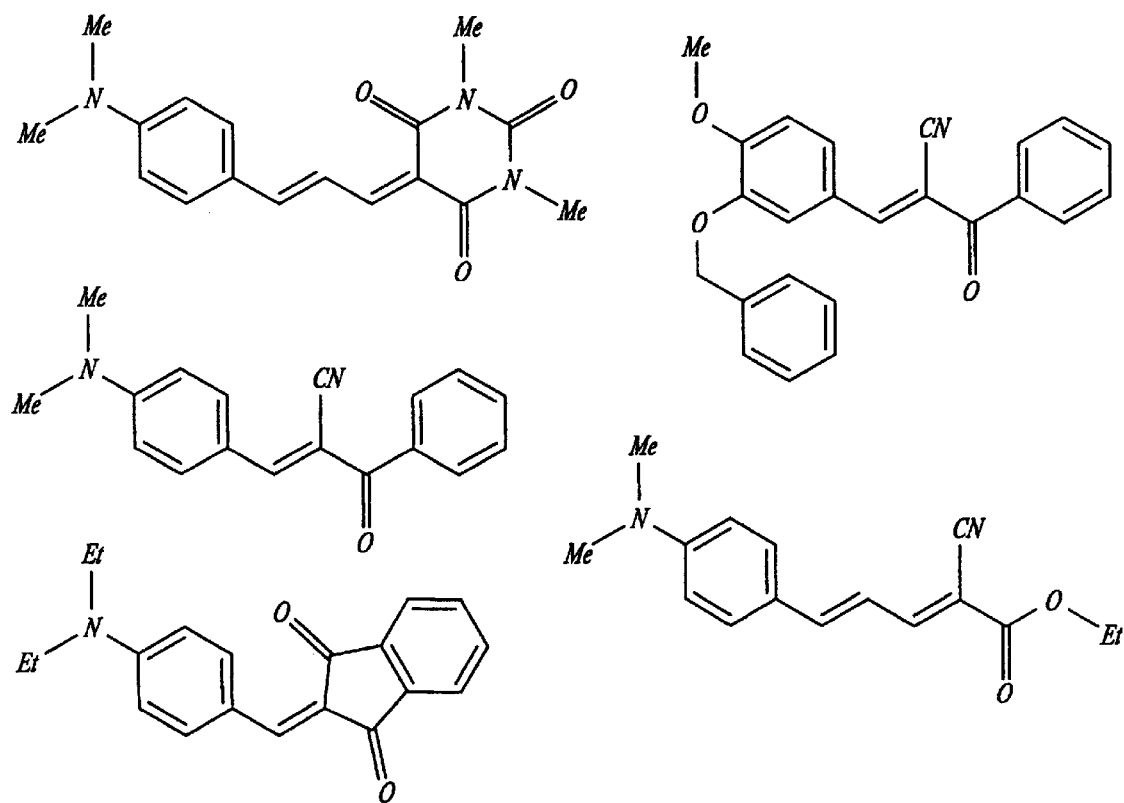
FIG. 5 illustrates chemical structures of preferred dyes used as optical probes in the methods of the present invention.

In preferred embodiments of the present invention, dyes used as optical probes are selected from the examples of dyes depicted in FIG. 5. While not intending to be bound by a single theory, applicant believes that these dyes operate as probes because the ground-state dye ($S_0$) absorbs a photon, promoting it to the singlet excited state ($S_1$). The excited dye then has two options for losing the energy absorbed, and the pathways are affected by the environment. In the simplest sense, if the $S_1$ state finds itself in a fluid, low-viscosity microenviromnent, it may rapidly lose energy to the environment by non-radiative processes, probably through twisting of the bonds between the donor and acceptor fragments of the dye. This is also affected by the free-volume of the environment, the molecular volume of the dye, and any interactions between the dye and the environment like hydrogen bonding (H-bonding) or polar interactions. If the dye is in a rigid, high-viscosity environment, then it will more slowly lose energy by dark-relaxation mechanisms, and with extended $S_1$ excited state lifetimes, fluorescence, (or loss of the energy by emission of a photon of lower energy than the originally absorbed photon) will become more likely. Often, the value K is defined as the 'quantum yield of fluorescence' in these systems, ranging from 0 to 1, defined as (# of photons emitted by fluorescence/# of photons absorbed by the dye). In the literature, depending of the dye environment and temperature, K will range from nearly 0 to nearly 1.0 for some of these dyes, for example, dyes 1 and 2.

Of course, the optical behavior of dye probes may be monitored by different techniques. For example, systems and methods can be employed for measuring the direct effects of the environment on dye absorption properties (absorptivity, color, solvatochromic effects, etc.), or the direct effects of the environment on dye-dye interactions, including excimer formation, dye aggregation, excited state quenching effects, etc. In other embodiments, systems and methods are employed to measure the diffusion rates of dyes, polymers, or other molecules, including covalently dye-labeled polymers, (not just simple dyes in a polymer matrix). For example, fluorescence polarization methods, where the dye is excited with polarized light, and the polarization of the emitted fluorescent light is measured, provide information about how rapidly the dye molecule is tumbling in space. Alternatively, forced-rayleigh scattering methods can be employed. This technique involves destroying a photobleachable dye in defined spaces within a sample, usually by a diffraction pattern of high-energy laser light to form a grating of dye in the sample, and detecting the diffusion of material in the sample with a low-energy laser that detects how this grating is smeared out and disappears with time. In other systems, the probe molecule is partitioned between phases to provide information about relative properties of the phases.

In another aspect of the invention, the systems and methods described herein are applied not only to screen properties of polymers or other organic materials with a small set of dyes, but they can also be applied to screen and optimize dyes for their usefulness with particular polymers or organic materials. In these embodiments, a single material, such as a polymer or organic material, is combined with an array of dyes at predefined locations on a substrate. Similar to the previous embodiment, the substrate is illuminated and heated, and the fluorescence response to illumination is detected for each library element. The dyes may then be compared for usefulness for a particular property of the polymer or organic material. For example, if the relevant property is the relative glass transition temperature of the polymer, the dyes may be compared to determine which dye provides the greatest break or change in slope at $T_g$ as the intensity of fluorescence emission is plotted with temperature.

III. Optical Systems

Optical systems for monitoring the optical behavior of probes or dyes will generally include a source of excitation radiation for directing the excitation radiation to the substrate and an optical measuring system for measuring emissions from each of the materials on the substrate. The optical measuring system usually includes a coupling (e.g., fiber optic) of each individual library element's luminescence to a photodetector, such as a high resolution spectrograph/CCD detector.

The excitation radiation source(s) may comprise immobilized or stationary point light sources, e.g., lasers such as argon, helium-neon, diode, dye, titanium sapphire, frequency-doubled diode pumped Nd:YAG and krypton. Other suitable light sources include halogen light sources, light emitting diodes, fiber optics, and the like. Typically, the light source illuminates the sample with an excitation wavelength that is within the visible, ultraviolet or infrared spectrums, but other wavelengths may be used depending on the application. In one embodiment, the light source will emit light having a red to near infrared wavelength, about 700–900 nanometers. This wavelength range has a relatively high sensitivity for many detectors, and it also allows the optics to filter light from other sources, such as the light from the room (which is typically in the 400 to 700 nanometer range).

The light from the point source is usually directed simultaneously at the entire substrate to facilitate parallel or rapid sequential screening of the array of materials. Alternatively, the light may be directed at a movable radiation direction system which rapidly scans the light beam back and forth across the surface of the substrate. A variety of devices may be employed to generate the sweeping motion of the light. For example, resonant scanners, rotating polygons or galvanometer devices may be employed to scan the light across the substrate. As used herein, the term "galvanometer" refers to devices that employ a servo motor to oscillate or rotate a mirror over a restricted, predefined range, which is typically less than 90°. This generates a rapidly sweeping or rastering beam reflecting from the galvanometer mirror, which is then directed at and swept across the surface of a substrate that is to be scanned. An optical train may also be employed between the light source and the galvanometer mirror to assist in directing, focusing or filtering the radiation directed at and reflected from the galvanometer mirror.

Optical detection is preferably accomplished by a sensor array that is positioned so as to receive emissions from the materials on the substrate. In one embodiment, the sensor array comprises a large area, research-grade charge-coupled device (CCD) detector (gated-intensified or non-intensified). Alternatively, the sensor array may comprise other conventional detectors, such as a photo detecting device having photocathodes and a video contact image.

In order to avoid the detrimental effects of reflected excitation radiation upon the detection of the fluorescence, dichroic mirrors or beam splitters may be included in the optical train between the substrate and the light detector. These dichroic beam splitters or mirrors are reflective to radiation in the wavelength of the excitation radiation while transmissive to radiation in the wavelength of the response radiation. Following separation of the response radiation from the reflected excitation radiation, the response radiation or fluorescence is then directed at a detector, e.g., CCD array, to measure the level of response radiation and record that level as a function of the position on the substrate from which that radiation originated. The response radiation may be focused upon the detector through a spatial filter such as a confocal pinhole. Such spatial filters reduce or eliminate unwanted signals from structures above and below the plane of focus of the excitation radiation. Additionally, the device may incorporate a bandpass filter between the dichroic mirror and the detector to further restrict the wavelength of radiation that is delivered to the detector.

Suitable methods for detecting fluorescently labeled materials can be found in U.S. Pat. No. 5,361,734 to Stern and International Application publication number WO 90/15070 to Pirrung, the complete disclosures of which are incorporated herein by reference.

The system of the present invention further includes a device for changing the environment of the substrate so that the optical properties of the probes change. In a preferred embodiment, this device comprises a temperature control system for varying the temperature of the substrate, and the probes and materials therewith. The temperature control system may comprise any suitable heating and/or cooling device, such as a heater plate, convection heater, a circulating bath, a refrigerated air circulating device, resistance heater, peltier device (thermoelectric cooler), or other temperature controller may be implemented.

V. EXAMPLES

Example 1

Figure 2:
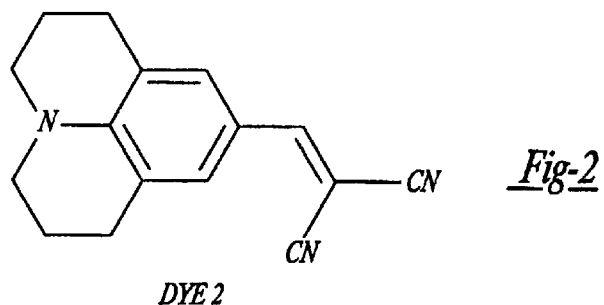
FIG. 2 illustrates the chemical structure of a second dye used as an optical probe in the methods of the present invention.
Figure 3:
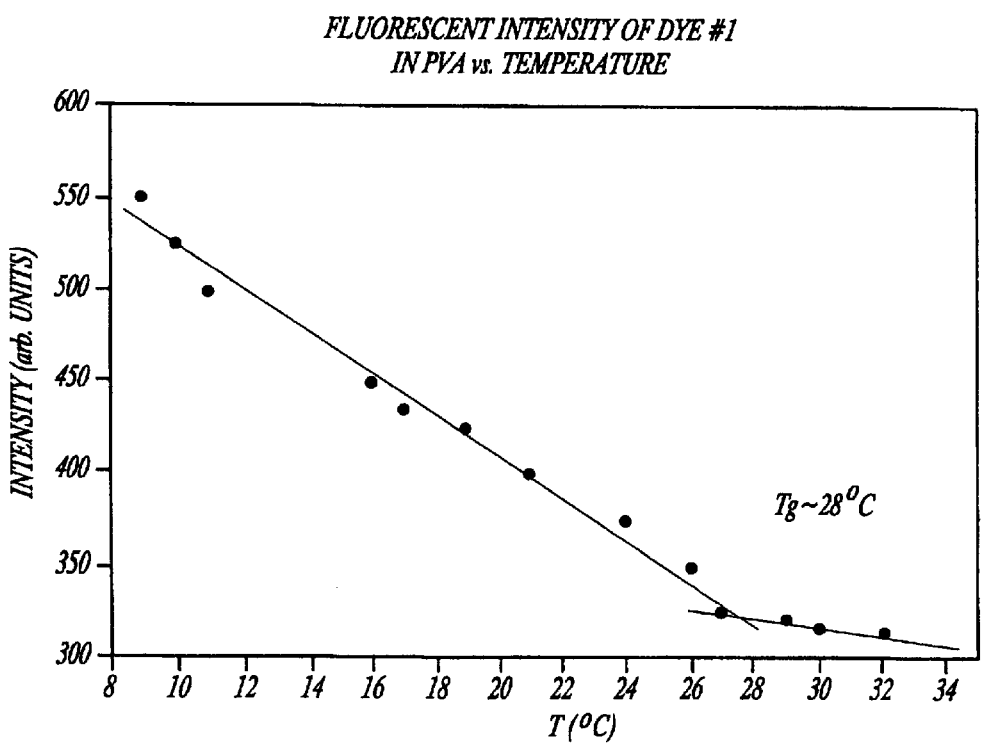
FIG. 3 is a graph of the fluorescence intensity as a function of temperature of the first dye shown FIG. 1.

A substrate of anodized aluminum was prepared with 1 cm$^2$ samples of 16 polymer films, comprising 4 polymers with independently measured $T_g$ values, by DSC, each with 2 dyes (dyes 1 and 2 in FIGS. 1 and 2, respectively) and at two film thicknesses. The polymers were poly(vinyl acetate), $T_g$=30° C., poly(methyl methacrylate), $T_g$=122° C., poly(ethyl methacrylate), Tg=63° C., and polystyrene, Tg =94° C. Films were cast with nominal thickness of 2 microns with an amount of each of the dyes to give a film absorbance of approximately 0.5, and at 10 microns thickness with an amount of each of the dyes to give a film absorbance of approximately 1.0. The fluorescent intensity was measured with a CCD camera equipped with a long-pass filter at 475 nm, under blue light excitation, as a function of temperature, using a thermoelectric heating element. Analysis of the temperature dependence of fluorescent intensity clearly shows the $T_g$ of the materials. The following plot gives data representative of data, with poly-vinyl acetate and dye 1 (see FIG. 3).

Example 2

A synthetic library of approximately 192 donor-acceptor dyes was prepared in two 96-well polypropylene plates, with 12 different electron donating fragments and 16 electron-accepting fragments, by combining in each well equimolar solutions of the appropriate aldehyde and the appropriate active methylene compounds. See FIGS. 4A–4C for structures of starting material fragments.

From these dyes, cast film polymer libraries were prepared by robotically combining an appropriate amount of a polymer solution of poly(methyl methacrylate, Tg =approximately 100° C. and dye solution, and casting the polymer solution on 55 mm square glass substrates prepared with 963 mm roughened circular patches, onto which the solutions were cast.

Example 3

A copolymer library at various polymer compositions is created by simultaneous batch polymerization of monomers in the following manner. In a 96-vessel glass lined reactor block, with 1 mL volume in each vessel, is added a mixture of monomer solution A (4% by weight methyl acrylate in ethyl acetate) and solution B (4% by weight methyl methacrylate in ethyl acetate), such that vessel 1 receives 0.480 mL solution A and 0.000 mL solution B, vessel 2 receives 0.475 mL solution A and 0.005 mL solution B, etc, until vessel 96 receives 0.000 mL solution A and 0.480 mL solution B. To each well is added azobis(isobutyronitrile) in ethyl acetate solution, at 1% by weight to monomer, the reaction block is sealed under nitrogen atmosphere, and the reaction heated to 80° C. for 12 h, with agitation of the solutions, yielding a copolymer library with 96 nominal compositions ranging from homopolymer poly(methyl acrylate) through homopolymer poly(methyl methacrylate). Small aliquots from each vessel in this library are diluted with a dye solution of dye 1, and the solutions are cast to form 3 mm diameter polymer films on a 54 mm×54 mm glass substrate. The substrate is simultaneously (or sequentially, e.g., scannned) illuminated and heated, in nitrogen atmosphere, from 0° C. to 135° C. over 30 minutes, and the fluorescent intensity from each library element is observed as a function of temperature, allowing measurement of the $T_g$ of each polymer in the library.

Example 4

A 88-member library (11 columns by 8 rows) is prepared similarly to example 3, by preparing a different copolymer composition (at 4 wt % in ethyl acetate) of methyl acrylate. A single polymer composition of methyl acrylate with methyl methacrylate is prepared in all 8 vessels of each column, with homopolymer poly(methyl acrylate) in column 1, and homopolymer poly(methyl methacrylate) in column 11, and copolymers ranging from 90:10 to 10:90 wt % in columns 2–10. After polymerization was complete, plasticizer compounds are added to each row, in the following manner:

row 1: none
row 2: 10 wt % to polymer of dibutyl phthalate
row 3: 20 wt % to polymer of dibutyl phthalate
row 4: 40 wt % to polymer of dibutyl phthalate
row 5: 10 wt % to polymer of tritolyl phosphate
row 6: 20 wt % to polymer of tritolyl phosphate
row 7: 40 wt % to polymer of tritolyl phosphate
row 8: 10 wt % to polymer each of dibutyl phthalate and tritolyl phosphate To each solution is also added an appropriate amount of dye 1, and films of each sample are cast on glass substrate as in example 3. The glass transition temperature of each film is measured optically as in example 3, heating from −40° C. to 130° C. over 40 minutes, showing the effects of polymer plasticization by the added solvents.

What is claimed is:

1. A method for screening an array of polymerized materials at predefined locations on a substrate comprising:
   preparing on a substrate a spatially defined array of different polymerized materials containing at least one environment-sensitive optical probe;
   subjecting said substrate to a temperature ramp that includes the glass transition temperatures of the polymerized materials; and
   simultaneously monitoring the optical behavior of each probe in response to the glass transition temperature of the polymerized materials within the array.

2. The method of claim 1 wherein the monitoring step includes the step of observing the optical probe under conditions that allow the parallel measurement of the absolute properties of the materials in the array.

3. The method of claim 1 wherein the monitoring step includes the step of observing the optical probe under conditions that allow the parallel measurement of the relative properties of the materials in the array.

4. The method of claim 1 wherein the monitoring step comprises;
   directing light onto the optical probes and materials in the array;
   changing the environment of the substrate; and
   measuring a property of each material as a function of the changed environment.

5. The method as recited in claim 1 wherein each optical probe is a dye.

6. The method as recited in claim 1 wherein said optical probe is an inorganic phosphor.

7. The method of claim 1 wherein the preparing step comprises:
   combining a array of materials with a dye to form a library of resulting materials; and
   casting the resulting materials onto predefined locations on a substrate.

8. The method as recited in claim 1 wherein the optical probes are monitored with a sensor array.

9. The method of claim 8 wherein the sensor array is selected from the group comprising: CCD measuring systems, UV measuring systems, visible measuring systems, and IR measuring systems.

10. The method as recited in claim 1 wherein said materials are amorphous.

11. The method as recited in claim 1 wherein said materials are crystalline.

12. The method as recited in claim 1 wherein said materials are pure.

13. The method as recited in claim 1 wherein said materials are a mixture.

14. The method as recited in claim 1 wherein said materials are bulk.

15. The method as recited in claim 1 wherein said materials include a particle of materials.

16. The method as recited in claim 1 wherein said materials include a thin film.

17. The method as recited in claim 1 wherein said materials include a dispersion of materials.

18. The method as recited in claim 1 wherein said materials include an emulsion of materials.

19. The method as recited in claim 1 wherein said materials include a solution of materials.

20. The method as recited in claim 1 wherein the array is comprised of at least 5 materials.

21. The method as recited in claim 1 wherein the array is comprised of at least 10 materials.

22. The method as recited in claim 1 wherein the array is comprised of at least 20 materials.

23. The method as recited in claim 1 wherein the array is comprised of at least 50 materials.

24. The method as recited in claim 1 wherein the array is comprised of at least 100 materials.

25. The method as recited in claim 1 wherein the array is comprised of at least 500 materials.

26. The method as recited in claim 1 wherein the array is comprised of at least 1,000 materials.

27. A system for screening an array of materials at predefined locations on a substrate comprising:
   an array of polymerized materials having an optical probe therein on said substrate;
   at least one environment-sensitive optical probe combined with each of the materials at the predefined locations on the substrate;
   a light source for directing light at each of the predefined locations on the substrate;
   a measurement system for monitoring the optical properties of the probe at each location to characterize one or more properties of each material on the substrate; and
   a system for controlling the environment of the substrate, wherein the properties of the materials are characterized as a function of the controlled environment.

28. The system as described in claim 27, wherein said environmental-sensitive optical probe is a dye.

29. The system as described in claim 27, wherein the system for controlling the environment is a temperature varying system.

30. The system as described in claim 27, wherein the measurement system comprises a sensor array for measuring a fluorescence intensity of each optical probe as a function of temperature.

31. The system as described in claim 27, wherein the measurement system is a CCD system.

32. The system as described in claim 27, wherein the measurement system is a UV system.

33. The system as described in claim 1, wherein said optical measurement system is a visible system.

34. The system as described in claim 1, wherein said optical measurement system is an IR system.

* * * * *